United States Patent
Seya et al.

(10) Patent No.: US 10,105,385 B1
(45) Date of Patent: Oct. 23, 2018

(54) ADJUVANT COMPOSITION

(71) Applicant: National University Corporation Hokkaido University, Sapporo-shi (JP)

(72) Inventors: Tsukasa Seya, Sapporo (JP); Misako Matsumoto, Sapporo (JP)

(73) Assignee: National University Corporation Hokkaido University (JP)

( * ) Notice: Subject to any disclaimer, the term of this patent is extended or adjusted under 35 U.S.C. 154(b) by 0 days.

(21) Appl. No.: 15/531,671

(22) PCT Filed: Dec. 1, 2015

(86) PCT No.: PCT/JP2015/083825
§ 371 (c)(1),
(2) Date: May 30, 2017

(87) PCT Pub. No.: WO2016/088784
PCT Pub. Date: Jun. 9, 2016

(30) Foreign Application Priority Data

Dec. 2, 2014 (JP) .................................. 2014-244421

(51) Int. Cl.
| | |
|---|---|
| *C12N 15/117* | (2010.01) |
| *A61K 31/7125* | (2006.01) |
| *A61K 39/00* | (2006.01) |
| *A61K 39/39* | (2006.01) |
| *A61P 35/00* | (2006.01) |

(52) U.S. Cl.
CPC ...... *A61K 31/7125* (2013.01); *A61K 39/0011* (2013.01); *A61K 39/39* (2013.01); *C12N 15/117* (2013.01); *A61P 35/00* (2018.01); *C12N 2310/17* (2013.01); *C12N 2310/315* (2013.01); *C12N 2760/18432* (2013.01)

(58) Field of Classification Search
CPC ......................... A61K 31/7125; C12N 15/117
See application file for complete search history.

(56) References Cited

U.S. PATENT DOCUMENTS 8,980,634 B2 * 3/2015 Miled .................. A61K 39/165
435/483
2013/0178611 A1 7/2013 Seya et al.

FOREIGN PATENT DOCUMENTS

WO WO 2008/065752 A1 6/2008
WO WO 2012/014945 A1 2/2012

OTHER PUBLICATIONS

Zuniga et al. (2007) Attenuated measles virus as a vaccine vector. Vaccine, Elsevier, Amsterdam, NL, 25(16), Mar. 29, 2007, pp. 2974-2983.
Extended European Search Report dated May 4, 2018 for European Application No. 15865520.9.
Itoh, Kiyoharu et al., "The Clathrin-Mediated Endocytic Pathway Participates in dsRNA-Induced IFN-β Production" The Journal of Immunology, 2008, pp. 5522-5529, vol. 181.
International Search Report for PCT/JP2015/083825 dated Feb. 23, 2016.

* cited by examiner

*Primary Examiner* — Brian A Whiteman
(74) *Attorney, Agent, or Firm* — Knobbe, Martens, Olson & Bear, LLP

(57) ABSTRACT

Provided is an adjuvant composition comprising a nucleic acid comprising a double-stranded RNA bound to a single-stranded DNA, the double-stranded RNA consisting of a nucleotide sequence of SEQ ID NO: 1 and its complementary sequence, the single-stranded DNA consisting of a nucleotide sequence of SEQ ID NO: 2. Also provided is a vaccine composition comprising the adjuvant composition and an antigen or an antigen component. The nucleic acid contained in the adjuvant composition is a chemically synthesizable nucleic acid having potent adjuvant activity and high safety.

9 Claims, 9 Drawing Sheets
Specification includes a Sequence Listing.

Fig. 1A cM362-140 (chemical compound)
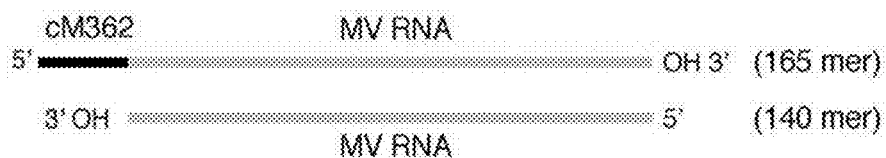
Fig. 1B
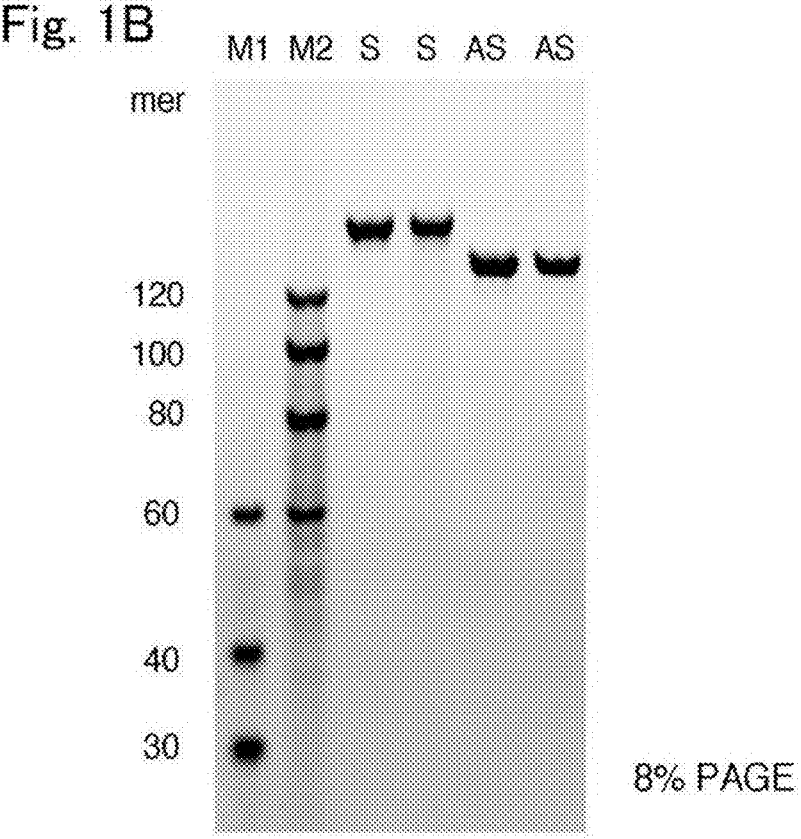
Fig. 2
cM362-139(IVT)
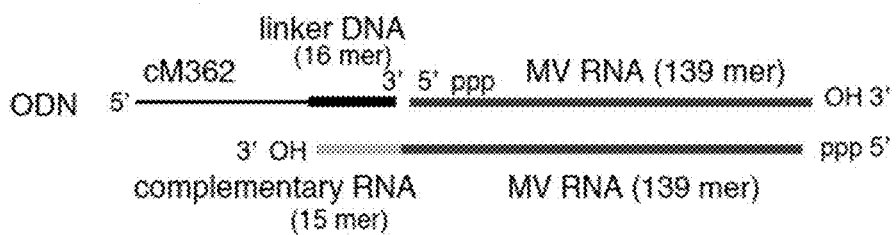

cM362-140 (chemical compound)

cM362-139 (IVT)

cM362-140 (chemical compound)

cM362-139 (IVT)

ADJUVANT COMPOSITION

CROSS REFERENCE TO RELATED APPLICATIONS

This application is a U.S. National Phase Application of PCT International Application Number PCT/JP2015/083825, filed on Dec. 1, 2015, designating the United States of America and published in the English language, which is an International Application of and claims the benefit of priority to Japanese Patent Application No. 2014-244421, filed Dec. 2, 2014. The disclosures of the above-referenced applications are hereby expressly incorporated by reference in their entireties.

REFERENCE TO SEQUENCE LISTING

A Sequence Listing submitted as an ASCII text file via EFS-Web is hereby incorporated by reference in accordance with 35 U.S.C. § 1.52(e). The name of the ASCII text file for the Sequence Listing is SeqList-IWAT006-001APC.txt, the date of creation of the ASCII text file is May 19, 2017, and the size of the ASCII text file is 7 KB.

TECHNICAL FIELD

The present invention relates to a novel adjuvant composition and a vaccine composition comprising the adjuvant composition.

BACKGROUND ART

Most cancer immunotherapies are conducted by administering a peptide vaccine as a cancer antigen. For increased efficacy, co-administration of a cancer antigen with an adjuvant that activates dendritic cells has been proposed. The present inventors have advanced research on adjuvants for cancer immunotherapies, and found that measles viral diRNA (defective interference RNA) functions as an adjuvant. In particular, the inventors have found that the diRNA induces IFN-β expression in human cells and enhances NK activity of NK cells, and that the diRNA administered together with a cancer antigen epitope induces marked tumor regression effect in cancer-bearing mice prepared by implanting B16 melanoma cells (Patent Literature 1). The inventors have also identified an oligo DNA that inhibits poly(I:C)-induced TLR3-mediated IFN-β expression, and reported that the oligo DNA shares the uptake receptor with poly(I:C) and the oligo DNA taken up in cells partially colocalized with TLR3 (Non Patent Literature 1). The inventors have designed a new nucleic acid based on the oligo DNA described in Non Patent Literature 1 and the diRNA described in Patent Literature 1, and discovered that the nucleic acid reaches endosomal TLR3 and exhibits potent adjuvant activity (Patent Literature 2).

Nucleic acids with adjuvant activity supplied as pharmaceuticals must comply with the GMP standard, and are hence required to be prepared by chemical synthesis. However, chemical synthetic techniques for long RNAs, such as those longer than 100 mer, have not yet been established, and such RNAs are synthesized solely by in vitro transcription. Under these circumstances, development of a chemically synthesizable nucleic acid with potent adjuvant activity and high safety has been greatly desired to provide an adjuvant formulation as a pharmaceutical for humans.

CITATION LIST

Patent Literature

Patent Literature 1: WO 2008/065752
Patent Literature 2: WO 2012/014945

Non Patent Literature

Non Patent Literature 1: The Journal of Immunology, 2008, 181: 5522-5529

SUMMARY OF INVENTION

Technical Problem

An object of the present invention is to provide an adjuvant composition comprising a chemically synthesizable nucleic acid having potent adjuvant activity and high safety, and a vaccine composition comprising the adjuvant composition and an antigen or an antigen component.

Solution to Problem

The present invention was made to solve the above problems and includes the following.
(1) An adjuvant composition comprising a double-stranded nucleic acid comprising a single-stranded nucleic acid A consisting of a nucleotide sequence of SEQ ID NO: 3 and a single-stranded nucleic acid B of SEQ ID NO: 4.
(2) The adjuvant composition according to the above (1), wherein the single-stranded nucleic acids A and B are chemically synthesized nucleic acids.
(3) The adjuvant composition according to the above (1) or (2), wherein the single-stranded nucleic acids A and B are formed of a plurality of chemically synthesized fragments linked by ligation.
(4) The adjuvant composition according to any one of the above (1) to (3), wherein the single-stranded nucleic acids A and B have no phosphate group attached to either of the ends.
(5) The adjuvant composition according to any one of the above (1) to (4), which comprises a single-stranded DNA whose nucleotides are all phosphorothioate modified.
(6) A vaccine composition comprising the adjuvant composition according to any one of the above (1) to (5) and an antigen or an antigen component.
(7) The vaccine composition according to the above (6), wherein the antigen is a cancer antigen.

Advantageous Effects of Invention

The present invention provides an adjuvant composition comprising a chemically synthesized nucleic acid having potent adjuvant activity and high safety. The nucleic acid is more stable and has fewer adverse effects than a conventional nucleic acid produced by in vitro transcription, and is thus very useful as an adjuvant for humans. The adjuvant composition may be combined with an antigen or an antigen component to provide an effective vaccine composition.

BRIEF DESCRIPTION OF DRAWINGS

FIG. 1A shows the structure of cM362-140, and FIG. 1B shows 7% urea-containing 8% PAGE of the sense and antisense RNAs of cM362-140.

FIG. 2 shows the structure of cM362-139.

DESCRIPTION OF EMBODIMENTS

Adjuvant Composition

Figure 3A:
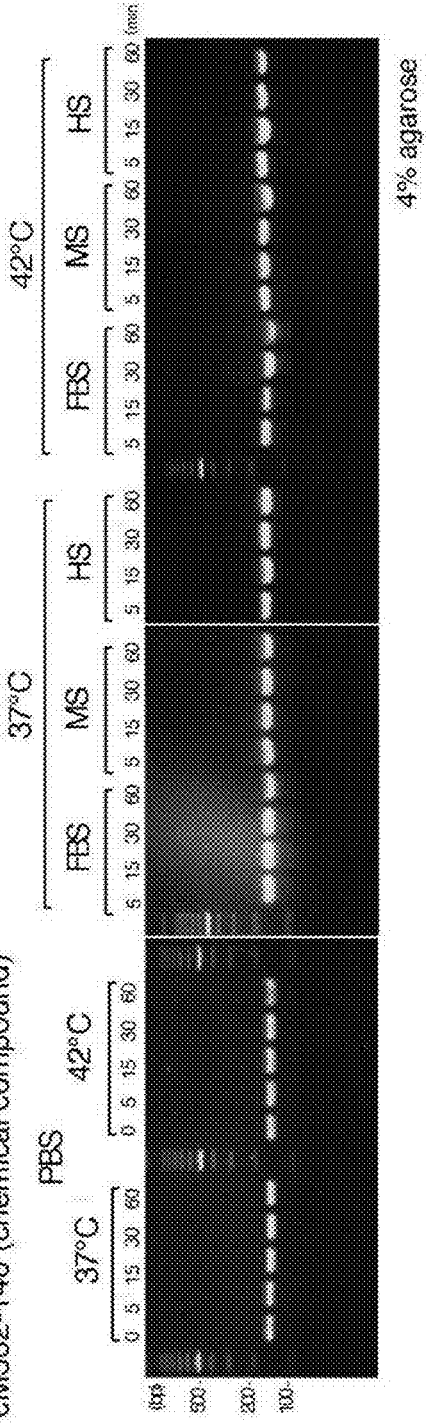
FIGS. 3A and 3B show the stability of cM362-140 and cM362-139 in serum-containing PBS, respectively.

The present invention provides an adjuvant composition comprising a nucleic acid comprising a double-stranded RNA bound to a single-stranded DNA, the double-stranded RNA consisting of a nucleotide sequence of SEQ ID NO: 1 and its complementary sequence, the single-stranded DNA consisting of a nucleotide sequence of SEQ ID NO: 2. The nucleic acid (hereinafter called "the nucleic acid of the present invention") contained in the adjuvant composition of the present invention is only required to comprise the double-stranded RNA bound to the single-stranded DNA, the double-stranded RNA consisting of a nucleotide sequence of SEQ ID NO: 1 and its complementary sequence, the single-stranded DNA consisting of a nucleotide sequence of SEQ ID NO: 2. It has been demonstrated that the double-stranded RNA portion of the nucleic acid of the present invention has the ability to activate TLR3, and that the single-stranded DNA portion is delivered to the endosomal compartments of dendritic cells. Therefore, the nucleic acid of the present invention is efficiently delivered to the endosomal compartments of dendritic cells and activates TLR3, thereby stimulating the immune function.

The nucleotide sequence of SEQ ID NO: 1 is the nucleotide residues at positions 1 to 140 in the nucleotide sequence (SEQ ID NO: 5) of the sense strand of diRNA of measles virus laboratory-adapted strain of Edmonston (ED). The nucleotide sequence complementary to SEQ ID NO: 1 is indicated in SEQ ID NO: 4. The single-stranded DNA consisting of the nucleotide sequence of SEQ ID NO: 2 may be joined to either strand of the double-stranded RNA. The single-stranded DNA may be directly joined to the double-stranded RNA, or alternatively the single-stranded DNA and the double-stranded RNA may be joined together via another nucleic acid (e.g., a linker nucleic acid). Preferably, the single-stranded DNA is directly joined to the double-stranded RNA. The 3' end of the single-stranded DNA may be joined to the 5' end of the RNA, or alternatively the 5' end of the single-stranded DNA may be joined to the 3' end of the RNA. More preferably, the 3' end of the single-stranded DNA is directly covalently bonded to the 5' end of the RNA. Further preferably, the 3' end of the single-stranded DNA is directly covalently bonded to the 5' end of the RNA sense strand (SEQ ID NO: 1). That is, the nucleic acid of the present invention is preferably composed of the single-stranded nucleic acid A consisting of the nucleotide sequence of SEQ ID NO: 3 (a chimeric nucleic acid composed of the single-stranded DNA and the RNA sense strand) and the single-stranded nucleic acid B of SEQ ID NO: 4 (the RNA antisense strand).

The nucleotides of the single-stranded DNA are preferably phosphorothioate-modified nucleotides (also called "sulfur-modified nucleotides"). Part or all of the nucleotides of the single-stranded DNA may be phosphorothioate modified, but preferably all of the nucleotides of the single-stranded DNA are phosphorothioate modified. Phosphorothioate modification increases nuclease resistance and enhances delivery to endosomal compartments.

The nucleic acid of the present invention is preferably formed of two nucleic acid strands produced by chemical synthesis. That is, the above single-stranded nucleic acids A and B are preferably chemically synthesized nucleic acid strands. Unlike conventional long RNAs synthesized by in vitro transcription, the nucleic acid of the present invention is produced by sequence-specific chemical synthesis, and thus is highly useful due to several advantages: for example, the nucleic acid of the present invention can be provided in a stable, lyophilized form, and has a correctly synthesized nucleotide sequence. The chemical synthesis method of the nucleic acid is not particularly limited, and a conventionally known chemical synthesis method can be appropriately used. Examples of the conventional method include the phosphoramidite method etc.

Each of the single-stranded nucleic acids may be chemically synthesized as a full-length nucleic acid. Alternatively, several fragments of each nucleic acid may be separately synthesized and linked by ligation to give the nucleic acid. The length (the number of bases) of each fragment is not particularly limited, but is preferably about 30 mer to about 80 mer, more preferably about 35 mer to about 70 mer, further preferably about 40 mer to about 60 mer. The ligation may be performed by a known ligation technique, and is preferably performed by ligation reaction mediated by a splint DNA, as described in, for example, Moore et al. (Moore MJ, & Sharp PA. Site-specific modification of pre-mRNA: the 2'-hydroxyl groups at the splice sites. Science 256: 992-997 (1992)) and Jing et al. (Jing Xu, Lapham J, & Crothers DM. Determining RNA solution structure by segmental isotopic labeling and NMR: Application to *Caenorhabditis elegans* spliced leader RNA 1. Proc. Natl. Acad. Sci. USA 93: 44-48 (1996)) (see Example 1).

Each of the single-stranded nucleic acids that are combined together to form the nucleic acid of the present invention preferably has no phosphate group at either of the ends. In in vitro transcription, synthesized RNA strands have triphosphoric acid attached to the 5' end, but since the nucleic acid of the present invention is produced by chemical synthesis, the single-stranded nucleic acids that are combined together to form the nucleic acid of the present invention have no phosphate group at the 5' end or the 3' end. If a nucleic acid having a phosphate group attached to the 5' end is administered to a living body at a high dose, the nucleic acid will activate the cytoplasmic RIG-I pathway to induce the production of a large amount of cytokines, and in turn will cause adverse effects (Robinson R A, DeVita V T, Levy H B, Baron S, Hubbard S P, Levine A S. A phase I-II trial of multiple-dose polyriboinosic-polyribocytidylic acid in patients with leukemia or solid tumors. J Natl Cancer Inst. 1976 September; 57(3): 599-602). In contrast, the nucleic acid of the present invention can be used to provide a highly safe adjuvant composition.

Unlike poly(I:C), the nucleic acid of the present invention preferentially activates the TICAM-1-mediated signaling system downstream of TLR3, and does not activate the intracellular RNA sensors other than TLR3. Hence, the nucleic acid of the present invention has been confirmed to have no risk of inducing cytokine storm and to be thus highly safe (see Examples 5 and 7). The nucleic acid of the present invention has also been confirmed to be more stable than a nucleic acid with a similar structure formed of RNA strands synthesized by in vitro transcription (see Example 2).

As described above, the nucleic acid of the present invention is delivered to the endosomal compartments of dendritic cells and activates TLR3, thereby enhancing various immune responses. The nucleic acid of the present invention is highly safe and stable, and is thus very useful as an active ingredient of an adjuvant composition. The adjuvant composition of the present invention can be formulated into a dosage form by appropriately blending the nucleic acid of the present invention with a pharmaceutically acceptable carrier or additive. In particular, the adjuvant composition can be formulated into an oral formulation, such as a tablet, a coated tablet, a pill, a powder, granules, a capsule, a solution, a suspension and an emulsion, or a parenteral formulation, such as an injection, an infusion, a suppository, an ointment and a patch. The amount of the carrier or additive to be added can be determined as appropriate based on the range typically used in the pharmaceutical field. The carrier or additive that may be added is not particularly limited and examples thereof include various types of carriers, such as water, physiological saline, other aqueous solvents, and aqueous or oily vehicles; and various types of additives, such as excipients, binders, pH adjusters, disintegrants, absorption promoters, lubricants, colorants, flavors and fragrances.

Examples of the additives that may be added to a tablet, a capsule, etc. include binders such as gelatin, corn starch, tragacanth and gum arabic; excipients such as crystalline cellulose; swelling agents such as corn starch, gelatin, and alginic acid; lubricants such as magnesium stearate; sweeteners such as sucrose, lactose and saccharin; and flavors such as peppermint flavor, wintergreen oil and cherry flavor. When the unit dosage form is a capsule, a liquid carrier such as oils and fats can be further added in addition to the above types of ingredients. A sterile composition for injection can be formulated in accordance with the usual pharmaceutical practice, for example, by dissolving or suspending the active ingredient in a vehicle, such as water for injection, or a natural vegetable oil, such as sesame oil and coconut oil. An aqueous liquid for injection that may be used is, for example, physiological saline or an isotonic solution containing glucose and/or other auxiliary substances (for example, D-sorbitol, D-mannitol, sodium chloride, etc.). The aqueous liquid for injection may be used in combination with an appropriate solubilizer, such as alcohols (e.g., ethanol), polyalcohols (e.g., propylene glycol, polyethylene glycol, etc.), and non-ionic surfactants (e.g., polysorbate 80™, HCO-50, etc.). An oily liquid that may be used is, for example, sesame oil or soybean oil. The oily liquid may be used in combination with a solubilizer such as benzyl benzoate and benzyl alcohol. Other additives that may be added are, for example, buffering agents (e.g., a phosphate buffer, a sodium acetate buffer, etc.), soothing agents (e.g., benzalkonium chloride, procaine hydrochloride, etc.), stabilizers (e.g., human serum albumin, polyethylene glycol, etc.), preservatives (e.g., benzyl alcohol, phenol, etc.) and antioxidants.

The formulations produced in the above manner can be administered to, for example, humans and other mammals (e.g., rats, mice, rabbits, sheep, pigs, cattle, cats, dogs, monkeys, etc.). The dose and dosing frequency of the adjuvant composition of the present invention can be determined, as appropriate, in accordance with the purpose of administration, the age, body weight, sex and past medical history of the subject, the mode of administration, etc.

Vaccine Composition

The present invention also provides a vaccine composition comprising the adjuvant composition of the present invention and an antigen or an antigen component. Examples of the antigen or the antigen component include a viral antigen, a bacterial antigen, a cancer antigen, a component thereof, etc. Preferred is a cancer antigen. Combined administration of the nucleic acid of the present invention and a cancer antigen has been revealed to induce marked tumor regression in tumor-bearing mice prepared by subcutaneously implanting cancer cells. Thus, the vaccine composition of the present invention has been confirmed to be very useful as a cancer vaccine. The vaccine composition of the present invention can be produced by adding an antigen or an antigen component to the adjuvant composition of the present invention. The vaccine composition of the present invention can be formulated into a dosage form in the same manner as in the dosage formulation of the adjuvant composition of the present invention.

Examples of the viral antigen include, for example, viral antigens from adenovirus, retrovirus, picornavirus, herpesvirus, rotavirus, hantavirus, coronavirus, togavirus, flavivirus, rhabdovirus, paramyxovirus, orthomyxovirus, bunyavirus, arenavirus, reovirus, papillomavirus, parvovirus, poxvirus, hepadnavirus, spongiform virus, HIV, CMV, hepatitis A virus, hepatitis B virus, hepatitis C virus, influenza virus, measles virus, poliovirus, smallpox virus, rubella virus, herpes simplex virus, varicella-zoster virus, Epstein-Barr virus, Japanese encephalitis virus, rabies virus, influenza virus, etc., or a combination thereof.

Examples of the bacterial antigen include, for example, bacterial antigens from *Bacillus* spp., *Escherichia* spp., *Listeria* spp., *Neisseria* spp., *Nocardia* spp., *Salmonella* spp., *Staphylococcus* spp., *Streptococcus* spp., etc., ora combination thereof.

Examples of the cancer antigen include, for example, cancer antigens from leukemia, lymphoma, astrocytoma, glioblastoma, melanoma, breast cancer, lung cancer, head and neck cancer, digestive system tumors, stomach cancer, colon cancer, liver cancer, pancreatic cancer, uterine cancer, ovarian cancer, vaginal cancer, testicular cancer, prostate cancer, penile cancer, bone tumors, blood vascular tumors, esophageal cancer, stomach cancer, rectal cancer, large intestine cancer, pancreatic cancer, gall bladder cancer, bile duct cancer, laryngeal cancer, lung cancer, bronchial cancer, bladder cancer, renal cancer, brain tumors, thyroid cancer, Hodgkin's disease, non-Hodgkin's lymphoma, multiple myeloma, etc., or a combination thereof.

The present invention further includes the following.

(1) A nucleic acid formed of the single-stranded nucleic acid A consisting of the nucleotide sequence of SEQ ID NO: 3 and the single-stranded nucleic acid B of SEQ ID NO: 4.

(2) A method for treating a cancer, comprising administering the nucleic acid according to the above (1) and a cancer antigen to a mammal.

(3) The nucleic acid according to the above (1) for use in the treatment of a cancer.

(4) Use of the nucleic acid according to the above (1) for the production of a therapeutic drug for a cancer.

EXAMPLES

The present invention will be described in more detail below with reference to Examples, but the present invention is not limited thereto.

Example 1: Preparation of Nucleic Acids (1) Preparation of cM362-140 (Chemically Synthesized Nucleic Acid)

The single-stranded nucleic acids (S1, S2, S3, AS1, AS2 and AS3) shown in Table 1 were synthesized by GeneDesign, Inc. The RNA fragments were chemically synthesized using tBDMS RNA amidites, the DNA fragment was chemically synthesized using standard DNA amidites, and phosphorothioate linkages (sulfur modification) were introduced using PADS. The synthesis was performed based on the phosphoramidite method (Scaringe, S. A. et al, J Am Chem 1998; 120: 11820-11821) using a solid-phase carrier with optimized parameters. After completion of the synthesis, the protecting groups on the bases and on the 2' position were removed by the usual method. The products were purified by reverse-phase HPLC and desalted to give the single-stranded nucleic acids.

T4 DNA ligase (Takara Bio) was added and the mixture was incubated at room temperature for 16 to 22 hours. The ligation reaction mixture contained 15.4 μM annealed complex, 66 mM Tris-HCl (pH 7.6), 6.6 mM $MgCl_2$, 10 mM DTT, 0.1 mM ATP and ~31 U/μL T4 DNA ligase. As the second ligation, S1 fragment (SEQ ID NO: 6, 40 nmol) and a splint DNA (SEQ ID NO: 13, 40-48 nmol) specific for the second ligation site were added to the first ligation reaction mixture, and hybridized in the same manner as in the first ligation. T4 DNA ligase was added and the mixture was incubated at room temperature for 16 to 22 hours. The second ligation reaction mixture contained 8.9 μM annealed complex, 66 mM Tris-HCl (pH 7.6), 6.6 mM $MgCl_2$, 10 mM of DTT, 0.1 mM of ATP and ~31 U/μL T4 DNA ligase. The derived full-length 165 mer sense RNA (single-stranded nucleic acid A) was isolated by 8% PAGE containing 7 M urea. After visualization by UV irradiation, the band of interest was excised and eluted with 0.3 M sodium acetate. The eluted RNA was ethanol precipitated and resuspended in RNase-free water. For large-scale preparation of the RNA, electro-elution was performed using D-tube Dialyzer Maxi (Novagen) and eluted RNA was dialyzed, concentrated and precipitated with ethanol. The concentration of RNA was determined by measuring the absorbance at 260 nm in a spectrometer. The yield was 8 to 10%.

To prepare the antisense RNA (single-stranded nucleic acid B) of cM362-140, three fragments, AS1 (SEQ ID NO: 9, 33 nmol), AS2 (SEQ ID NO: 10, 33 nmol) and AS3 (SEQ ID NO: 11, 33 nmol) and two splint DNAs (SEQ ID NOs: 14 and 15, 33 nmol each) specific for two different ligation sites were mixed, and hybridized. T4 DNA ligase was added and the mixture was incubated at room temperature for 16 to 22 hours. The ligation reaction mixture contained 15 μM annealed complex, 66 mM Tris-HCl (pH 7.6), 6.6 mM $MgCl_2$, 10 mM DTT, 0.1 mM ATP and ~31 U/μL T4 DNA

TABLE 1

| Fragment RNA | Sense MV-RNA sequence | Antisense MV-RNA sequence |
| --- | --- | --- |
| S1 (SEQ ID NO: 6) | 5'-t*g*c*t*g*c*t*g*c*t*t*g*c*a*a*g*c*a*g*c*t*t*g*a*t + MV(ED)DI RNA 1-14 | |
| S2 (SEQ ID NO: 7) | 5'-p + MV(ED)DI RNA 15-74 | |
| S3 (SEQ ID NO: 8) | 5'-p + MV(ED)DI RNA 75-140 | |
| AS1 (SEQ ID NO: 9) | | MV(ED)DI RNA 1013-1064 |
| AS2 (SEQ ID NO: 10) | | 5'-p + MV(ED)DI RNA 1065-1104 |
| AS3 (SEQ ID NO: 11) | | 5'-p + MV(ED)DI RNA 1105-1152 |

Bases in lower-case letters are oligodeoxynucleotides.

*, phosphorothioate; 5'-p, 5' phosphate.

The chemically synthesized long RNA cM362-140 was constructed by ligation reactions mediated by a splint DNA as described below (references: Moore MJ & Sharp PA. Site-specific modification of pre-mRNA: the 2'-hydroxyl groups at the splice sites. Science 256: 992-997 (1992), and Jing Xu, Lapham J, & Crothers DM. Determining RNA solution structure by segmental isotopic labeling and NMR: Application to *Caenorhabditis elegans* spliced leader RNA 1. Proc. Natl. Acad. Sci. USA 93: 44-48 (1996)).

To prepare the sense RNA (single-stranded nucleic acid A) of cM362-140, the ligation reactions were performed in two steps. As the first ligation, S2 fragment (SEQ ID NO: 7, 40 nmol), S3 fragment (SEQ ID NO: 8, 40 nmol) and a splint DNA (SEQ ID NO: 12, 40-48 nmol) specific for the ligation site were mixed, heated at 95° C. for 5 minutes and then slowly cooled to 4° C. to allow hybridization to take place.

ligase. The derived full-length 140 mer antisense RNA (single-stranded nucleic acid B) was purified by the same procedure as in the preparation of the sense RNA. The yield was 15 to 22%.

To generate cM362-140, the sense RNA (single-stranded nucleic acid A) and the antisense RNA (single-stranded nucleic acid B) were annealed. FIG. 1A shows the structure of cM362-140, and FIG. 1B shows 8% PAGE of the 165 mer sense RNA (single-stranded nucleic acid A) and the 140 mer antisense RNA (single-stranded nucleic acid B) synthesized above. The sense and antisense RNAs were each detected as a single band with a size consistent with the nucleotide length.

(2) Preparation of Control Nucleic Acid cM362-139

The structure of cM362-139 is shown in FIG. 2, and the nucleotide sequence of cM362-139 is shown in Table 2.

TABLE 2

DNA sequence of ODN (sODN and linker DNA) (SEQ ID NO: 16)
5'-t g c t g c t g c t t g c a a g c a g c t t g a t accgtggtcatgctcc-3'
Sense MV-RNA sequence (SEQ ID NO: 17)    Antisense MV-RNA sequence (SEQ ID NO: 18)

| GGG + MV (ED) DI RNA 1-136 | MV (ED) DI RNA 1017-1152 + cccggagcaugaccacgg |
|---|---|

^: phosphorothioate

The single-stranded DNA (ODN+linker DNA) was synthesized by GeneDesign, Inc. The defective interference RNA (diRNA) of measles virus (MV) laboratory-adapted strain of Edmonston(ED) was used as the template of the double-stranded RNA. DNA fragments covering this region of the MV genome and the T7 promoter sequence were amplified by PCR using the plasmid pCR-T7 MV as a template. The primers used are shown below.
ODN-139 Sense RNA (5' Primer)
  5'-tgtaatacgactcactatagggaccagacaaagctggga-3' (SEQ ID NO: 19)
T7 promoter sequence is underlined.
ODN-139 Sense RNA (3' Primer)
  5'-ggatacagtgccctgattaa-3' (SEQ ID NO: 20)
ODN-139 Antisense RNA (5' Primer)
  5'-tgtaatacgactcactataggatacagtgccctgattaa-3' (SEQ ID NO: 21)
T7 promoter sequence is underlined.
ODN-139 Antisense RNA (3' Primer)
  5'-ccgtggtcatgctccgggaccagacaaagctggga-3' (SEQ ID NO: 22)

The sense and antisense RNAs were in vitro transcribed from the PCR products using AmpliScribe™ T7 transcription kit (Epicentre Technologies) in accordance with the manufacturer's protocol. The transcribed products were isolated by 8% PAGE containing 7 M urea and purified in the same manner as in Example 1. Finally, the single-stranded DNA (ODN+linker DNA) and the sense and antisense RNAs were mixed and annealed to give cM362-139.

Example 2: Stability of Nucleic Acids (1) Stability in Serum-Containing PBS
cM362-140 and cM362-139 were separately dissolved at 20 μg/mL in serum-free PBS, PBS containing 10% heat-inactivated fetal bovine serum (FBS), PBS containing 10% mouse serum (MS) or PBS containing 10% human serum (HS), and incubated at 37° C. or 42° C. for 60 minutes. Aliquots containing 0.1 μg of the treated nucleic acids were taken before start of incubation (0 minute-incubation, only for serum-free PBS) and after 5-, 15-, 30- and 60-minute incubation, mixed with 10× loading dye (Takara Bio), and electrophoresed on 4% agarose gel (Nusieve 3:1 Agarose, Lonza) containing ethidium bromide.

Figure 3B:
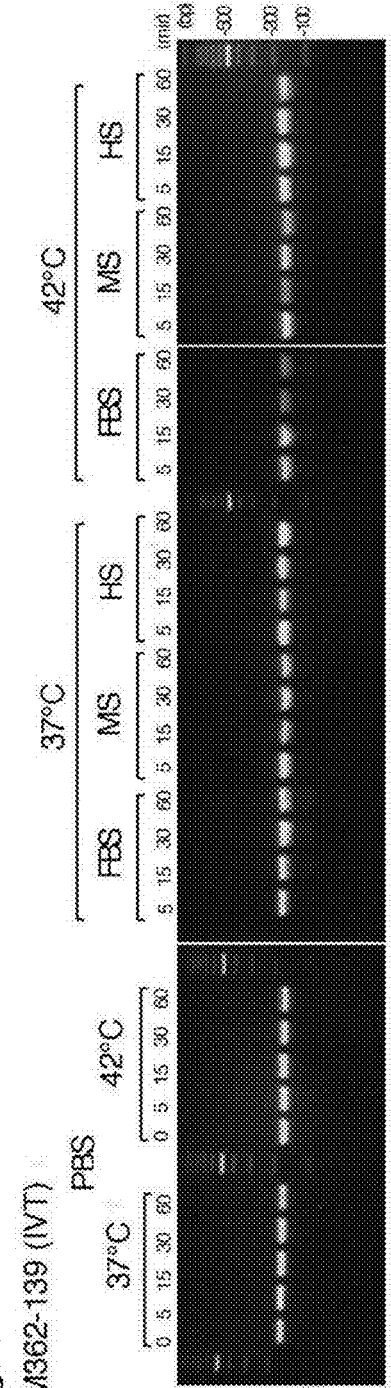

The results are shown in FIGS. 3A and 3B. FIGS. 3A and 3B show the electrophoretic patterns of cM362-140 and cM362-139, respectively. Both nucleic acids were stable during the 30-minute incubation at 37° C., but cM362-139, which was prepared by in vitro transcription, was slightly degraded during the 30-minute incubation in PBS containing serum (FBS, MS or HS) at 42° C.

(2) Stability in RNase-Free Water Containing Serum
The stability of the nucleic acids was examined by electrophoresis on 3% agarose gel using RNase-free water instead of PBS under the same conditions as above.

Figure 4A:
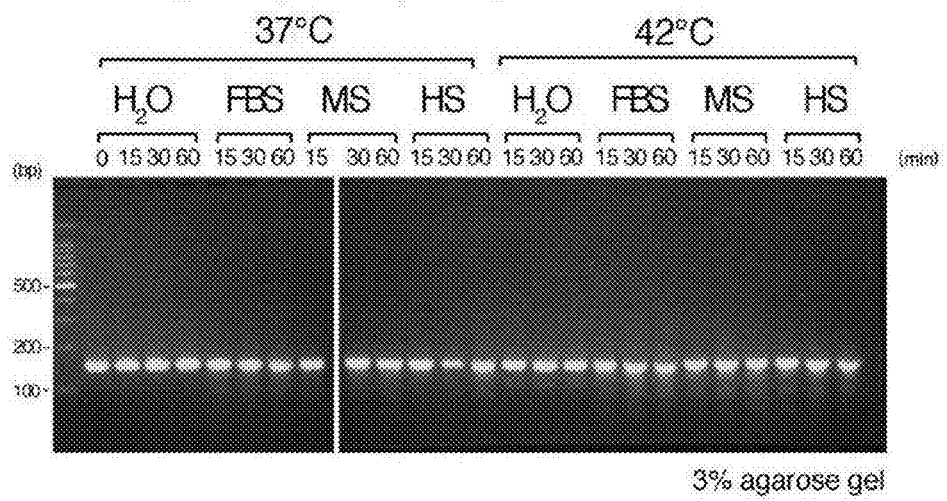
FIGS. 4A and 4B show the stability of cM362-140 and cM362-139 in RNase-free water containing serum, respectively.
Figure 4B:
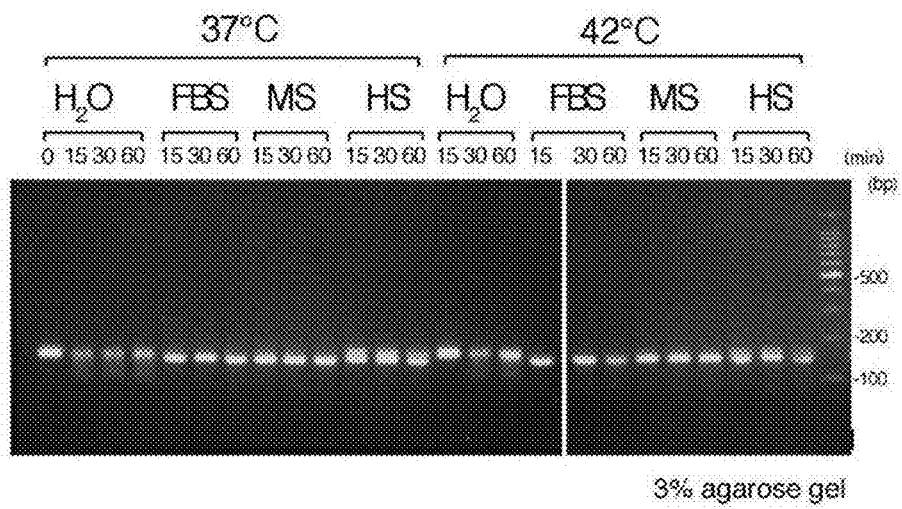

The results are shown in FIGS. 4A and 4B. FIGS. 4A and 4B show the electrophoretic patterns of cM362-140 and cM362-139, respectively. cM362-140 was stable under all the conditions, but cM362-139 was slightly degraded during incubation in the presence of serum (FBS, MS or HS).

Thus, cM362-140 was found to be more stable than cM362-139.

Example 3: Activation of IFN-β Promoter

HEK293 cells ($8 \times 10^5$ cells/well) were seeded in 6-well culture plates. The HEK293 cells were transfected with a human TLR3 expression vector (400 ng/well) or an empty vector (400 ng/well) together with a reporter plasmid p-125 (400 ng/well) and an internal control vector phRL-TK (20 ng/well, Promega) using Lipofectamine 2000 (Invitrogen). The reporter plasmid p-125 containing the human IFN-β promoter region (−125 to +19) was provided by Dr. Taniguchi (the University of Tokyo). Dulbecco's Modified Eagle's medium (DMEM, Invitrogen) supplemented with 10% heat-inactivated fetal bovine serum (FCS, Invitrogen) and antibiotics was used as medium.

Twenty-four hours after transfection, the cells were recovered, resuspended in medium and seeded in 96-well culture plates. The nucleic acids, i.e., cM362-140, cM362-139, poly(I:C) (Amersham) and the double-stranded RNA portion (dsRNA140) of cM362-140, were separately added to a concentration of 10 μg/mL in the following manner:
(A) each nucleic acid was directly added to medium containing HEK293 cells expressing human TLR3,
(B) each nucleic acid and DOTAP liposomal transfection reagent (Roche) were added to medium containing HEK293 cells expressing human TLR3, or
(C) each nucleic acid and Lipofectamine 2000 (Invitrogen) were added to medium containing HEK293 cells.

Dual-Luciferase Reporter Assay System (Promega) was used for luciferase activity measurement. The luciferase activity was measured 6 hours after addition of the nucleic acids in (A) and (B) and 24 hours after addition of the nucleic acids in (C).

Figure 5:
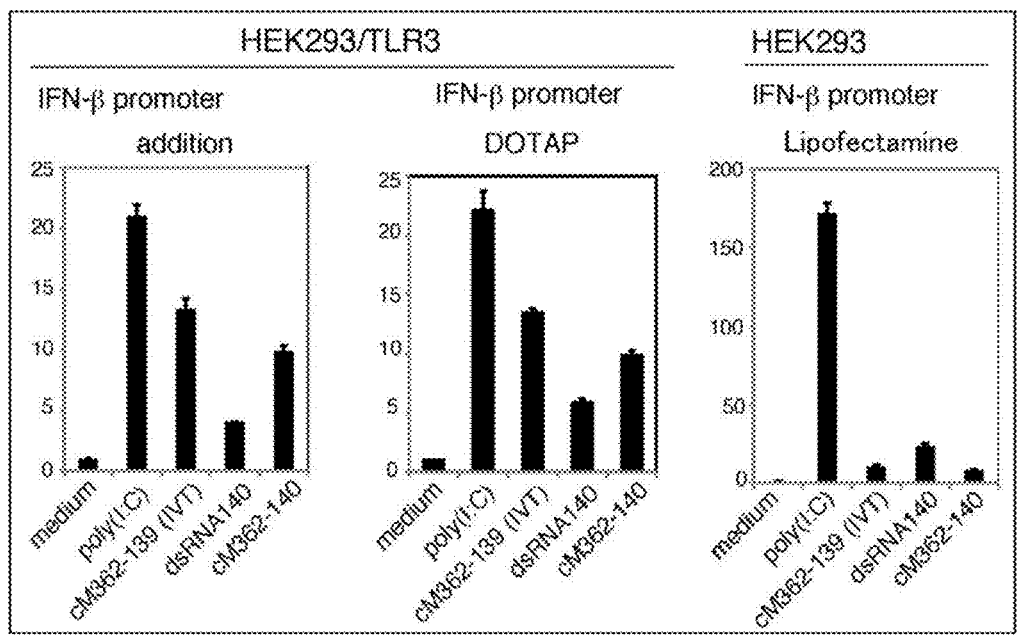
FIG. 5 shows IFN-β promoter activation by cM362-140 as evaluated by reporter assay.

The results are shown in FIG. 5. The left panel shows the results of (A), the center panel shows the results of (B) and the right panel shows the results of (C). The data were expressed as the mean value±SD (n=3). cM362-140 efficiently induced IFN-β promoter activation similar to cM362-139 in (A) the simple addition of cM362-140 to the extracellular matrix (medium) of the HEK293 cells expressing human TLR3, and in (B) the endosomal delivery of cM362-140 to the HEK293 cells expressing human TLR3 (FIG. 5, left and center panels). Activation of the IFN-β promoter was not observed in (C) the cytoplasmic delivery of cM362-140 to the HEK293 cells not expressing human TLR3. The results indicate that cM362-140 induces TLR3-mediated IFN-β promoter activation but does not induce other IFN-β promoter activation via other RNA/DNA sensors.

Example 4: Induction of In Vitro Cytokine Production

The spleen was harvested from wild-type C57BL/6J mice (WT) and TLR3 knockout mice (TLR3KO) (provided by Dr.

Akira, Osaka University), and treated with collagenase. The splenocyte suspension was passed through a filter, erythrocytes were lysed, and the splenocytes were washed with medium. The splenocytes were subjected to MACS system (Miltenyi Biotech) using anti-CD11c microbeads to isolate CD11c$^+$ cells as splenic DCs. Dulbecco's Modified Eagle's medium (DMEM, Invitrogen) supplemented with 10% heat-inactivated fetal bovine serum (FCS, Invitrogen) and antibiotics was used as medium. All the animal experiments herein were performed according to the guideline is sued by the Hokkaido University Animal Care and Use Committee.

The splenic DCs were seeded at $5 \times 10^5$ cells in 500 µL of medium per well in 24-well plates, then 20 µg/mL nucleic acid (cM362-140, cM362-139, poly(I:C), or dsRNA140) was added (A) alone, (B) together with DOTAP liposomal transfection reagent (Roche), or (C) together with Lipofectamine 2000 (Invitrogen), and the cells were cultured for 24 hours. After 24 hours of culture, the culture supernatants were recovered, and the production levels of TNF-α, IL-6 and IFN-β were measured. BD CBA Flex Set system was used for measurement of TNF-α and IL-6, and Mouse IFN-β ELISA Kit (PBL Assay Science) was used for measurement of IFN-β.

Figure 6:
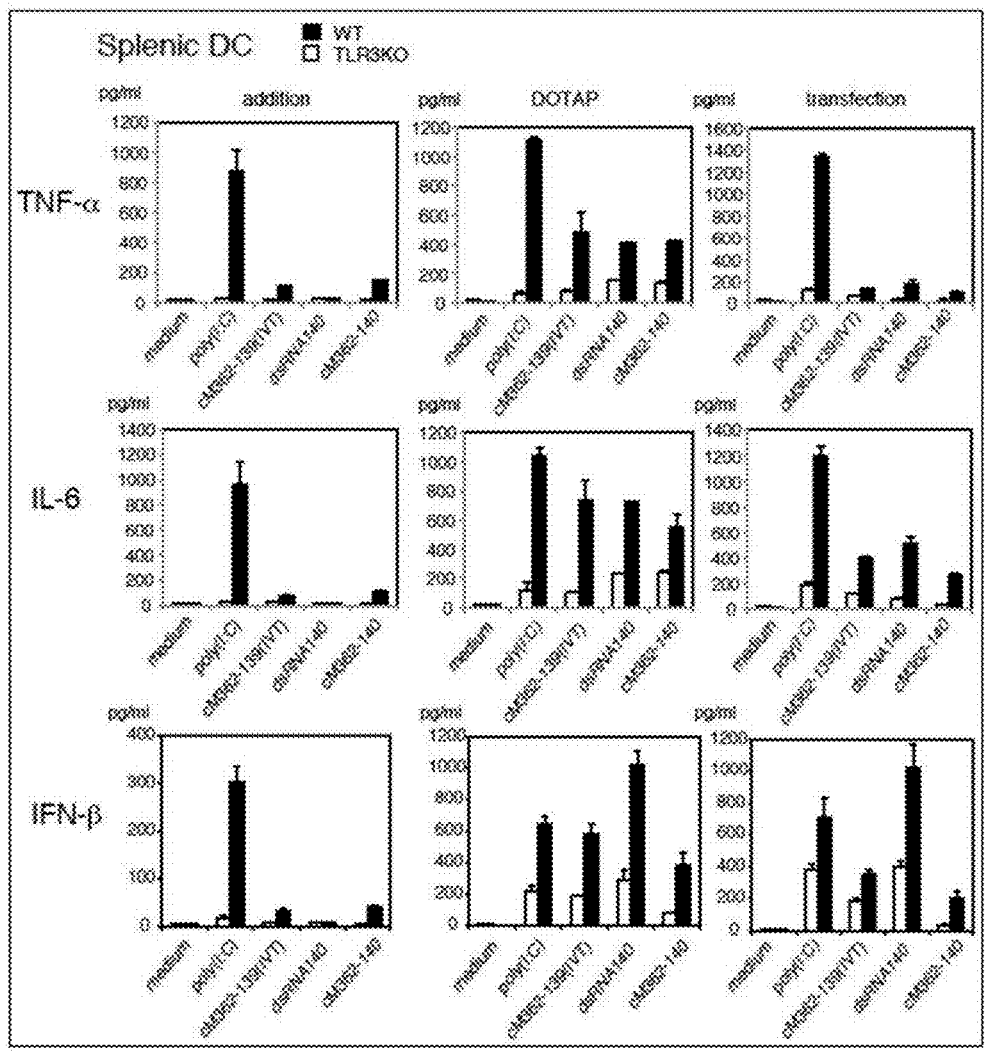
FIG. 6 shows cytokine production induced by cM362-140 as evaluated in vitro using splenic dendritic cells from wild-type mice and TLR3 knockout mice.

The results are shown in FIG. 6. The left panels show the production levels in the case of (A) the addition of the nucleic acid alone to the medium, the center panels show the production levels in the case of (B) the addition of the nucleic acid and DOTAP liposomal transfection reagent, and the right panels show the production levels in the case of (C) the addition of the nucleic acid and Lipofectamine 2000. The upper panels show TNF-α production, the middle panels show IL-6 production, and the lower panels show IFN-β production. The data from three independent experiments were expressed as the mean value±SD. As is clear from the results shown in the left panels, extracellular addition of cM362-140 alone to the splenic DCs induced a subtle increase in TNF-α, IL-6 and IFN-β production in the splenic DCs from the wild-type mice. As shown in the results in the center panels, endosomal delivery of cM362-140 using DOTAP liposomal transfection reagent induced an increase in TNF-α, IL-6 and IFN-β production in the splenic DCs from the wild-type mice. On the other hand, as apparent from the results in the right panels, when cM362-140 was delivered to the cytoplasm using Lipofectamine 2000, the production levels of TNF-α, IL-6 and IFN-β were lower than those in the endosomal delivery. No induction of cytokine production by cM362-140 was observed in the splenic DCs from the TLR3KO mice in either delivery condition. The results indicate that cM362-140 targets the endosomal TLR3, but does not target the cytoplasmic RNA/DNA sensors.

Example 5: Induction of In Vivo Cytokine Production

Fifty micrograms of cM362-140, cM362-139 or poly(I:C) was intraperitoneally administered to wild-type C57BL/6J mice (9 weeks old, female) or TLR3KO mice (9 weeks old, female). Three mice were used per group. Each of the nucleic acids was prepared as a solution in RNase-free water. At 1 hour, 3 hours, and 6 hours after nucleic acid administration, the blood was collected from the tail vein, and the serum levels of TNF-α, IL-6 and IL-10 were measured. BD CBA Flex Set system was used for the measurement.

Figure 7:
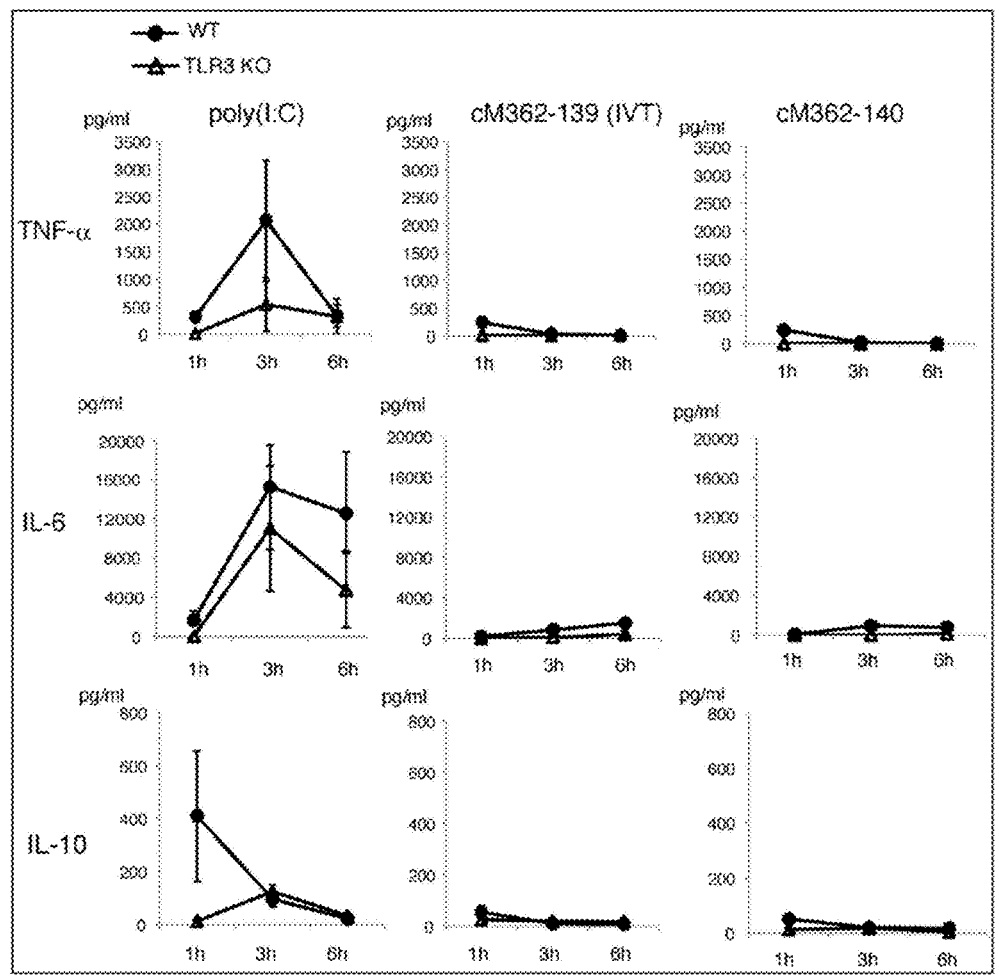
FIG. 7 shows cytokine production induced by intraperitoneal administration of cM362-140 to wild-type mice and TLR3 knockout mice as evaluated in vivo.

The results are shown in FIG. 7. The left panels show poly(I:C) administration, the center panels show cM362-139 administration, and the right panels show cM362-140 administration. The upper panels show TNF-α production, the middle panels show IL-6 production, and the lower panels show IL-10 production. The data were expressed as the mean value±SE (n=3). As apparent from FIG. 7, the in vivo cytokine production levels induced by cM362-140 were markedly low as compared with those induced by poly(I:C). The results indicate that cM362-140 has no risk of causing adverse effects such as cytokine storm when administered to a living body and is highly safe.

Example 6: Induction of Antigen-Specific CTL (1) Tumor Regression Effect

C57BL/6J mice were shaved at the back, and $2 \times 10^6$ EG7 cells (cancer cells established from EL4 cells from thymic carcinoma of C57BL/6 mice by forced expression of ovalbumin antigen) in 200 µL of PBS were subcutaneously implanted to establish tumors. Tumor volumes (cm$^3$=(long diameter)×(short diameter)$^2$×0.4) were measured over time. Day 8 after implantation (tumor volume: about 0.6 cm$^3$), cM362-140 alone, OVA alone, or cM362-140+OVA was subcutaneously administered around the tumor. As a control, PBS (−) alone was administered in the same manner. Four mice were used per group. cM362-140 and OVA were at doses of 50 µg and 100 µg, respectively, and were prepared as a solution in PBS (−). The dosing volume was 50 µL. Seven days after the first administration (day 15 after implantation), the second administration was performed. Endotoxin-free OVA (Hyglos) was used as OVA.

Figure 8:
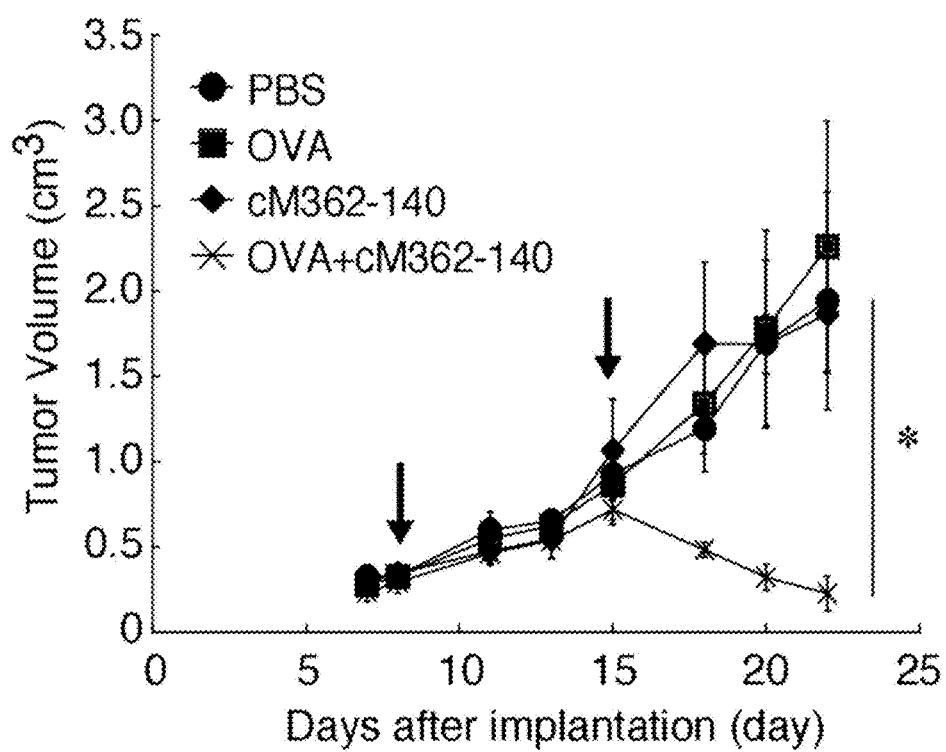
FIG. 8 shows the tumor regression effect of cM362-140 and/or OVA in wild-type mice bearing EG7 cell tumors.

The results are shown in FIG. 8. The cM362-140 single administration group induced barely any regression of the tumors, whereas the cM362-140+OVA administration group induced significant tumor regression (*: p<0.05). The data were expressed as the mean value±SE, and the statistical analysis was performed by one-way ANOVA with Bonferroni's test.

(2) Tetramer Assay

The tetramer assay was performed using spleen cells prepared from mice bearing EG7 tumors to evaluate the adjuvant activity of cM362-140. Spleen cells were prepared by the usual method seven days after the second administration of PBS, cM362-140 alone, OVA alone, or cM362-140+OVA in the above (1) (at day 22 after implantation). The spleen cells were dyed with FITC-CD8α (BioLegend), PerCP/Cy5.5-7AAD (BD Biosciences), APC-CD3ε (BioLegend) and PE-OVA-Tetramer (MBL) to detect OVA-specific CD8$^+$ T cells (tetramer$^+$/CD8$^+$/CD3$^+$ cells), and the proportion of the cells was calculated.

Figure 9:
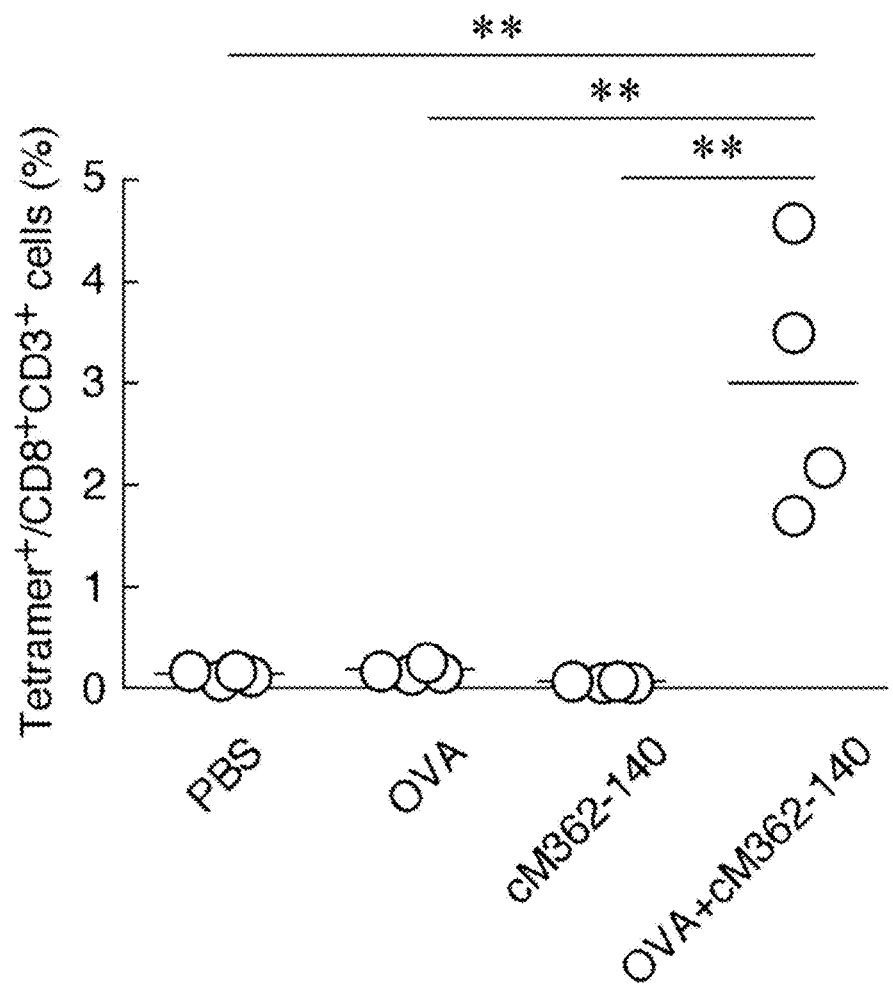
FIG. 9 shows the detection of OVA-specific CD8⁺ T cells in spleen cells after administration of cM362-140 and/or OVA to wild-type mice bearing EG7 cell tumors.

The results are shown in FIG. 9. As is clear from FIG. 9, the proportion of OVA-specific CD8$^+$ T cells in spleen cells was significantly large in the cM362-140+OVA administration group, as compared with those in the other groups (**: p<0.01). The statistical analysis was performed by one-way ANOVA with Bonferroni's test.

(3) IFN-γ Production

The spleen cells prepared in the above (2) were seeded in 96-well culture plates ($2 \times 10^6$ cells in 200 µL per well). The cells were cultured in the presence of 100 nM OVA peptide (SL8) for 3 days, and the IFN-γ levels in the culture supernatants were measured by BD CBA Flex Set System.

Figure 10:
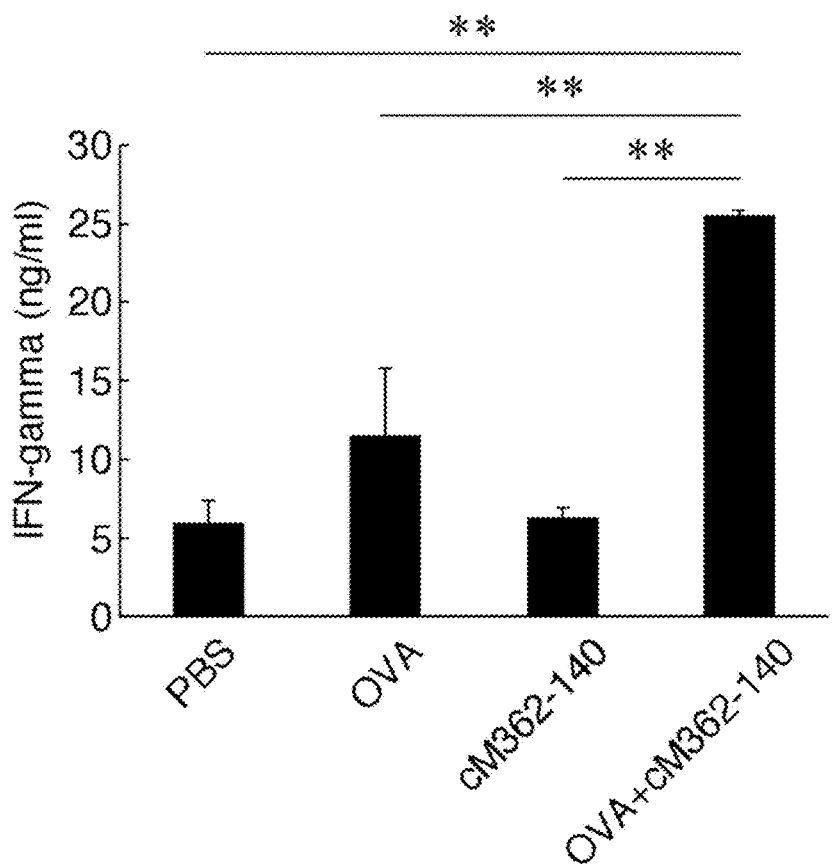
FIG. 10 shows the production levels of IFN-γ in spleen cells after administration of cM362-140 and/or OVA to wild-type mice bearing EG7 cell tumors.

The results are shown in FIG. 10. As is clear from FIG. 10, the IFN-γ production level in spleen cells was significantly large in the cM362-140+OVA administration group, as compared with those in the other groups (**: p<0.01). The data were expressed as the mean value±SE, and the statistical analysis was performed by one-way ANOVA with Bonferroni's test.

(4) Summary

The results in Example 6 indicate that cM362-140 induces the proliferation and activation of antigen-specific cytotoxic T cells, and serves as an effective adjuvant when used together with a cancer antigen.

Example 7: Tumor Regression Effect Via Activation of NK Cells

Regression of implanted cancer induced by activation of NK cells was evaluated using a C57BL/6-B16 syngeneic NK-sensitive tumor-implant model (Akazawa T., T. Ebihara, M. Okuno, Y. Okuda, K. Tsujimura, T. Takahashi, M. Ikawa, M. Okabe, T. Ebihara, M. Shingai, N. Inoue, M. Tanaka-Okamoto, H. Ishizaki, J. Miyoshi, M. Matsumoto, and T. Seya. 2007. Antitumor NK activation induced by the Toll-like receptor 3-TICAM-1 (TRIF) pathway in myeloid dendritic cells. Proc. Natl. Acad. Sci. USA. 104: 252-257.). Wild-type C57BL/6J mice (WT) and TICAM-1 knockout mice (TICAM-1 KO, established by the inventors) were shaved at the back, and $6 \times 10^5$ B16 melanoma cells (B16D8) in 200 µL of PBS were subcutaneously implanted to establish tumors. Tumor volumes ($cm^3$=(long diameter)×(short diameter)$^2$×0.4) were measured over time. Day 12 after implantation, distilled water (DW) or 150 µg of cM362-140 mixed with in vivo-JetPEI was subcutaneously administered around the tumor. Three mice were used per group.

Figure 11:
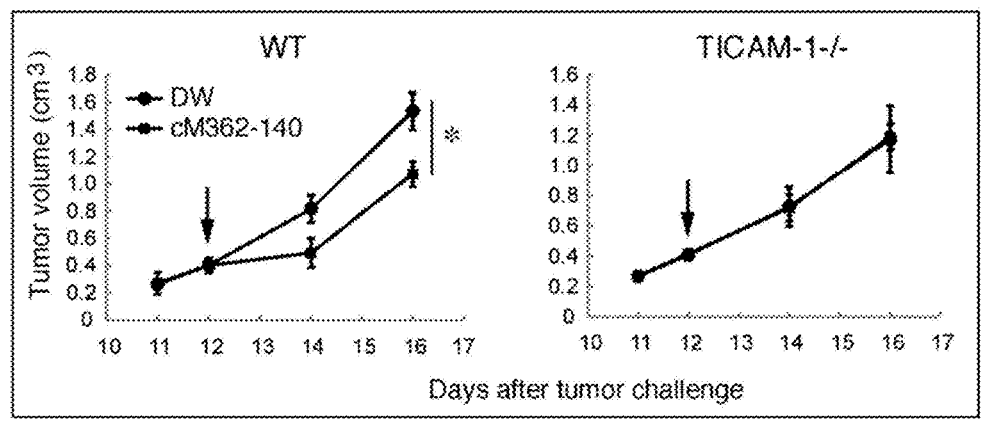
FIG. 11 shows the tumor regression effect of cM362-140 in mice (wild-type mice or TICAM-1 knockout mice) bearing B16 melanoma cell (B16D8) tumors.

The results are shown in FIG. 11. The left panel shows tumor volumes in the wild-type mice, and the right panel shows tumor volumes in the TICAM-1 KO mice. As apparent from FIG. 11, significant tumor regression effect was observed in the wild-type mice that received cM362-140 compared with the group with distilled water (DW) administration. No tumor regression effect was observed in the TICAM-1 KO mice. The results indicate that the nucleic acid of the present invention exhibits its effect via TICAM-1-mediated signaling.

The present invention is not limited to each of the embodiments and Examples described above, and various modifications are possible within the scope of the claims. Embodiments obtainable by appropriately combining the technical means disclosed in the different embodiments of the present invention are also included in the technical scope of the present invention. The contents of the scientific literature and the patent literature cited herein are hereby incorporated by reference in their entirety.

The invention claimed is:

1. An adjuvant composition comprising a double-stranded nucleic acid comprising a first single-stranded nucleic acid A consisting of a nucleotide sequence of SEQ ID NO: 3 and a second single-stranded nucleic acid consisting of a nucleotide sequence of SEQ ID NO: 4.

2. The adjuvant composition according to claim 1, wherein the first and second single-stranded nucleic acids are chemically synthesized nucleic acids.

3. The adjuvant composition according to claim 1, wherein the first and second single-stranded nucleic acids are formed of a plurality of chemically synthesized fragments linked by ligation.

4. The adjuvant composition according to claim 1, wherein the first and second single-stranded nucleic acids have no phosphate group attached to either of the ends.

5. The adjuvant composition according to claim 1, wherein said first and/or said second single-stranded nucleic acids comprise nucleotides that are phosphorothioate modified.

6. A vaccine composition comprising the adjuvant composition according to claim 1 and an antigen or an antigen component.

7. The vaccine composition according to claim 6, wherein the antigen is a cancer antigen.

8. A nucleic acid comprising a first single-stranded nucleic acid with a nucleotide sequence of SEQ ID NO: 3 and a second single-stranded nucleic acid with a nucleotide sequence of SEQ ID NO: 4.

9. A method of inhibiting a cancer in a mammal comprising administering the nucleic acid as defined in claim 8 and a cancer antigen to a mammal.

* * * * *

SEQUENCE LISTING

```
<160> NUMBER OF SEQ ID NOS: 22

<210> SEQ ID NO 1
<211> LENGTH: 140
<212> TYPE: RNA
<213> ORGANISM: Measles virus

<400> SEQUENCE: 1
accagacaaa gcuggaaua gaaacuucgu auuucaaag uuuucuuuaa uauauugcaa      60
auaaugccua accaccuagg gcaggauuag gguuccggag uucaaccaau uaguccuuaa     120
ucagggcacu guauccgacu                                                140

<210> SEQ ID NO 2
<211> LENGTH: 25
<212> TYPE: DNA
<213> ORGANISM: Artificial
<220> FEATURE:
<223> OTHER INFORMATION: synthetic DNA

<400> SEQUENCE: 2
tgctgctgct tgcaagcagc ttgat                                          25

<210> SEQ ID NO 3
<211> LENGTH: 165
<212> TYPE: DNA
<213> ORGANISM: Artificial
<220> FEATURE:
<223> OTHER INFORMATION: DNA/RNA chimeric molecule for cM362-140
<220> FEATURE:
<221> NAME/KEY: misc_feature
<222> LOCATION: (26)..(165)
<223> OTHER INFORMATION: RNA

<400> SEQUENCE: 3
tgctgctgct tgcaagcagc ttgataccag acaaagcugg gaauagaaac uucguauuuu     60
caaaguuuuc uuuaauauau ugcaaauaau gccuaaccac cuagggcagg auuaggguuc    120
cggaguucaa ccaauuaguc cuuaaucagg gcacuguauc cgacu                   165
```

-continued

<210> SEQ ID NO 4
<211> LENGTH: 140
<212> TYPE: RNA
<213> ORGANISM: Measles virus

<400> SEQUENCE: 4
agucggauac agugcccuga uuaaggacua auugguugaa cuccggaacc cuaauccugc 60
ccuagguggu uaggcauuau uugcaauaua uuaaagaaaa cuuugaaaau acgaaguuuc 120
uauucccagc uuugucuggu 140

<210> SEQ ID NO 5
<211> LENGTH: 1152
<212> TYPE: RNA
<213> ORGANISM: Measles virus

<400> SEQUENCE: 5
accagacaaa gcugggaaua gaaacuucgu auuuucaaag uuuucuuuaa uauauugcaa 60
auaaugccua accaccuagg gcaggauuag gguuccggag uucaaccaau uaguccuuaa 120
ucagggcacu guauccgacu aacuugccua acaaagauac uauagagaag cuagaggaau 180
uggcagccau cuuaucgaug gcucugcucc ugggcaaaau aggaucaaua cuggugauua 240
agcuuaugcc uuucagcggg gauuuuguuc agggauuuau aaguuaugua gggucucauu 300
auagagaagu gaaccuugua uacccuagau acagcaacuu cauaucuacu gaaucuuauu 360
ugguuaugac agaucucaag gcuaaccggc uaaugaaucc ugaaaagauu aagcagcaga 420
uaauugaauc aucugugagg acuucaccug gacuuauagg ucacauccua uccauuaagc 480
aacuaagcug cauacaagca auugugggag acgcaguuag uagaggugau aucaauccua 540
cucugaaaaa acuuacaccu auagagcagg ugcugaucaa uugcggguug gcaauuaacg 600
gaccuaagcu gugcaaagaa uugauccacc augauguugc cucagggcaa gauggauugc 660
uuaauucuau acucauccuc uacagggagu uggcaagauu caaagacaac caaagaaguc 720
aacaagggau guuccacgcu uaccccguau ugguaaguag caggcaacga gaacuuauau 780
cuaggaucac ccgcaaauuu ugggggcaca uucuucuuua cuccgggaac agaaaguuga 840
uaaauaaguu uauccagaau cucaaguccg gcuaucugau acuagacuua caccagaaua 900
ucuucguuaa gaaucuaucc aagucagaga aacagauuau uaugacgggg gguuugaaac 960
gugagugggu uuuuaaggua acagucaagg agaccaaaga augguauaag uuagucggau 1020
acagugcccu gauuaaggac uaauugguug aacuccggaa cccuaauccu gcccuaggug 1080
guuaggcauu auuugcaaua uauuaaagaa aacuuugaaa auacgaaguu ucuauuccca 1140
gcuuugucug gu 1152

<210> SEQ ID NO 6
<211> LENGTH: 39
<212> TYPE: DNA
<213> ORGANISM: Artificial
<220> FEATURE:
<223> OTHER INFORMATION: DNA/RNA chimeric molecule for cM362-140
<220> FEATURE:
<221> NAME/KEY: misc_feature
<222> LOCATION: (26)..(39)
<223> OTHER INFORMATION: RNA

<400> SEQUENCE: 6
tgctgctgct tgcaagcagc ttgataccag acaaagcug 39

<210> SEQ ID NO 7
<211> LENGTH: 60
<212> TYPE: RNA
<213> ORGANISM: Measles virus

<400> SEQUENCE: 7
ggaauagaaa cuucguauuu ucaaaguuuu cuuuaauaua uugcaaauaa ugccuaacca 60

<210> SEQ ID NO 8
<211> LENGTH: 66
<212> TYPE: RNA
<213> ORGANISM: Measles virus

<400> SEQUENCE: 8
ccuagggcag gauuaggguu ccggaguuca accaauuagu ccuuaaucag ggcacuguau 60
ccgacu 66

<210> SEQ ID NO 9
<211> LENGTH: 52
<212> TYPE: RNA
<213> ORGANISM: Measles virus

<400> SEQUENCE: 9
agucggauac agugcccuga uuaaggacua auugguugaa cuccggaacc cu 52

<210> SEQ ID NO 10
<211> LENGTH: 40
<212> TYPE: RNA
<213> ORGANISM: Measles virus

<400> SEQUENCE: 10
aauccugccc uaggugguua ggcauuauuu gcaauauauu 40

<210> SEQ ID NO 11
<211> LENGTH: 48
<212> TYPE: RNA
<213> ORGANISM: Measles virus

<400> SEQUENCE: 11
aaagaaaacu uugaaaauac gaaguuucua uucccagcuu ugucuggu 48

<210> SEQ ID NO 12
<211> LENGTH: 30
<212> TYPE: DNA
<213> ORGANISM: Artificial
<220> FEATURE:
<223> OTHER INFORMATION: splint DNA

<400> SEQUENCE: 12
cgaagtttct attcccagct ttgtctggta 30

<210> SEQ ID NO 13
<211> LENGTH: 30
<212> TYPE: DNA
<213> ORGANISM: Artificial
<220> FEATURE:
<223> OTHER INFORMATION: splint DNA

<400> SEQUENCE: 13
taatcctgcc ctaggtggtt aggcattatt 30

<210> SEQ ID NO 14
<211> LENGTH: 30

```
<212> TYPE: DNA
<213> ORGANISM: Artificial
<220> FEATURE:
<223> OTHER INFORMATION: splint DNA

<400> SEQUENCE: 14
acctagggca ggatttagggt tccggagttc                                    30

<210> SEQ ID NO 15
<211> LENGTH: 30
<212> TYPE: DNA
<213> ORGANISM: Artificial
<220> FEATURE:
<223> OTHER INFORMATION: splint DNA

<400> SEQUENCE: 15
ttcaaagttt tctttaatat attgcaaata                                     30

<210> SEQ ID NO 16
<211> LENGTH: 41
<212> TYPE: DNA
<213> ORGANISM: Artificial
<220> FEATURE:
<223> OTHER INFORMATION: synthetic DNA for cM362-139

<400> SEQUENCE: 16
tgctgctgct tgcaagcagc ttgataccgt ggtcatgctc c                        41

<210> SEQ ID NO 17
<211> LENGTH: 139
<212> TYPE: RNA
<213> ORGANISM: Artificial
<220> FEATURE:
<223> OTHER INFORMATION: in vitro transcriptional RNA for cM362-139

<400> SEQUENCE: 17
gggaccagac aaagcuggga auagaaacuu cguauuuuca aaguuuucuu uaauauauug    60
caaauaaugc cuaaccaccu agggcaggau uagggguuccg gaguucaacc aauuagaccu   120
uaaucagggc acuguaucc                                                 139

<210> SEQ ID NO 18
<211> LENGTH: 154
<212> TYPE: RNA
<213> ORGANISM: Artificial
<220> FEATURE:
<223> OTHER INFORMATION: in vitro transcriptional RNA for cM362-139

<400> SEQUENCE: 18
ggauacagug cccugauuaa ggacuaauug guugaacucc ggaacccuaa uccugcccua    60
ggugguuagg cauuauuugc aauauauuaa agaaaacuuu gaaaauacga aguuucuauu    120
cccagcuuug ucugguccg gagcaugacc acgg                                 154

<210> SEQ ID NO 19
<211> LENGTH: 39
<212> TYPE: DNA
<213> ORGANISM: Artificial
<220> FEATURE:
<223> OTHER INFORMATION: Primer

<400> SEQUENCE: 19
tgtaatacga ctcactatag ggaccagaca aagctggga                           39

<210> SEQ ID NO 20
```

```
<211> LENGTH: 20
<212> TYPE: DNA
<213> ORGANISM: Artificial
<220> FEATURE:
<223> OTHER INFORMATION: Primer

<400> SEQUENCE: 20
ggatacagtg ccctgattaa                                                       20

<210> SEQ ID NO 21
<211> LENGTH: 39
<212> TYPE: DNA
<213> ORGANISM: Artificial
<220> FEATURE:
<223> OTHER INFORMATION: Primer

<400> SEQUENCE: 21
tgtaatacga ctcactatag gatacagtgc cctgattaa                                  39

<210> SEQ ID NO 22
<211> LENGTH: 35
<212> TYPE: DNA
<213> ORGANISM: Artificial
<220> FEATURE:
<223> OTHER INFORMATION: Primer

<400> SEQUENCE: 22
ccgtggtcat gctccgggac cagacaaagc tggga                                      35
```